United States Patent [19]

Peterson

[11] Patent Number: 5,756,114
[45] Date of Patent: May 26, 1998

[54] METHOD AND COMPOSITION FOR TERMITE CONTROL

[76] Inventor: James E. Peterson, 923 NE. Hazelfern Pl., Portland, Oreg. 97232

[21] Appl. No.: 536,661

[22] Filed: Sep. 29, 1995

[51] Int. Cl.⁶ .................................................. A01N 25/08
[52] U.S. Cl. ................ 424/405; 424/410; 424/DIG. 11; 514/312; 514/600
[58] Field of Search ............................. 424/405, DIG. 11, 424/409, 410, DIG. 10; 514/312, 600

[56] References Cited

U.S. PATENT DOCUMENTS

| | | | |
|---|---|---|---|
| 4,873,084 | 10/1989 | Sallay | 424/658 |
| 5,024,832 | 6/1991 | Omata et al. | 424/84 |
| 5,166,193 | 11/1992 | Levin et al. | 514/23 |
| 5,329,726 | 7/1994 | Thorne et al. | 43/124 |
| 5,609,879 | 3/1997 | Myles | 424/410 |

OTHER PUBLICATIONS

PDR Dapsone–Jacobus Pharmaceutical p. 1079, 1990 44th Edition.

Su, N. et al., "Suppression of Foraging Populations of the Formosan Subterranean Termite (Isoptera: Rhinotermitidae) by Field Applications of a Slow–Acting Toxicant Bait," 84 *J. Econ. Entomol.*, 1525–1531 (1991).

Robertson, A.S., et al., "Discovery of an Effective Slow–Acting Insect Growth Regulator For Controlling Subtertanean Termites," 50 *Down To Earth*, 1–7, (1995).

Angus Chemical Company Technical Data Sheet: Amical (1993).

Biology of Termites, Moore et al., Academic Press, vol. 1, 1969, pp. 423–432.

Characterization of Slow–acting Insecticides for the Remedial Control of the Formosan Subterranean Termite (Isoptera: Rhinotermitidae), Su et al., Journal of Economic Entomology, vol. 80, No. 1, 1987, pp. 1–4.

Toxicity and Feeding Deterrency of a Dihaloalkyl Arylsulfone Biocide, A–9248, Against the Formosan Subterranean Termite (Isoptera: Rhinotermitidae), Su et al., Entomological Society of America, vol. 81, No. 3, 1988, pp. 850–854.

Amebicides, Sulfones, American Society of Hospital Pharmacists, Inc., Sept. 1976, pp. 35–36, 482–486.

Protozoa Associated with Termites and Their Role in Digestion, Honigberg, at least as early as Oct. 28, 1994, pp. 1–33.

Pesticide Chemistry in the 20th Century, ACS Symposium Series; 37 ISSN 0097–6156, 1977, pp. 212–213.

Production ecology of ants and termites, J.P. La Fage, Cambridge University Press 1978, International Biological Programme 13, pp. 188–223.

Nourishment and Evolution in Insect Societies, Hunt et al., Westview Press, 1994, pp. 152–153.

Termites in the Humid Tropics, Uttangi et al., U N E S C O, Oct. 1960, pp. 155–161.

The Functions of Carbohydrates in Insect Life Processes, Chippendale, Academic Press, Inc. 1978, pp. 14–15.

*Primary Examiner*—Neil S. Levy

[57] ABSTRACT

A composition for termite control including a pesticide that is toxic to a termite's gut-dwelling cellulase-producing protozoa is disclosed. The pesticide is present at an effective pesticidal and non-feeding-deterrent concentration. The composition preferably includes a termite attractant and is impregnated in a cellulose-containing material which is thereafter exposed to foraging worker termites. The worker termites are attracted preferentially to the impregnated material and consume it, thereby ingesting the pesticide which they then feed to the other members of the termite colony.

6 Claims, 1 Drawing Sheet

METHOD AND COMPOSITION FOR TERMITE CONTROL

BACKGROUND AND SUMMARY OF THE INVENTION

This invention relates to a method and composition for the control of termites.

Established colonies of foraging subterranean termites, for example Reticulitermes spp and *Coptotermes formosanus*, are difficult to eradicate. Although foraging worker termites distribute food to the other members of the colony, providing a pesticide for the worker termites to consume is typically ineffective in eliminating the colony because of the feeding behavior of the worker termites. When the pesticide level in material is very high the worker termites will not feed on the material at all. Furthermore, if the termite does ingest material containing a very high level of pesticide, the ingesting termite dies, but typically before the pesticide can be passed on to any other members of the colony. The surviving colony members merely replace the lost worker. In addition, after contact with certain lower concentrations of a pesticide the worker termites learn to avoid feeding at the lower pesticide concentration and the pesticide serves as a feeding deterrent.

If the colony can be found, one known method of eliminating the colony involves saturating the ground containing the nest and foraging galleries with a pesticide. Such a procedure, however, requires special chemical applicators for injecting the pesticide into the ground. This method is extremely expensive. It is also undesirable because an extensive area will consequently be contaminated with a pesticide residue.

In order to prevent a termite infestation, structure builders often put several kilograms of pesticides in the soil under and around the structure to form a toxic chemical barrier against foraging termites. Such an application, however, does nothing to eliminate the termite population in the soil, so that any breach in the barrier leaves the structure vulnerable to termites. This method also results in a toxic pesticide residue in the surrounding soil. In addition, in homes protected with the barrier toxin chlorpyrifos, the current barrier toxin of choice for domestic pest controllers, researchers can demonstrate a residual concentration of chlorpyrifos in the air within the home more than five years after the initial application of the pesticide. Furthermore, the aerial concentration of the toxin in the home is greatest near the floor, where small children may play.

Worker termites forage for food at random, marking or remarking each trail with a pheromone, which is a chemical signal substance produced by the termite. For example, termites of the species *Coptotermes formosanus* and *Reticulitermes flavipes* respond to (Z,Z,E)-3,6,8-dodecatrien-1-ol, an active principal of a trail pheromone secreted by the sternal gland of the termites. By its nature, a trail-marking pheromone has a very low vapor pressure because in order to be effective it must remain where it is deposited. Thus, the attractive range of the pheromone (Z,Z,E)-3,6,8-dodecatrien-1-ol is less than the length of a single termite.

Omata et al. U.S. Pat. No. 5,024,832 discloses a method, and a composition including the trail-marking pheromone (Z,Z,E)-3,6,8-dodecatrien-1-ol, for marking a trail to lead termites to a capturing adhesive, or to lead termites to a 0.1–40% pesticide solution. The composition, however, has a very low rate of diffusion away from the marked area, and thus has an effective range equal only to about the length of a termite. In addition, the method is ineffective for eliminating an infesting termite colony because of the high concentration of pesticide offered to the foraging worker termites. The worker termites will avoid completely the higher levels of the pesticide, and will learn to avoid the pesticide at the lower levels.

Thorne et al. U.S. Pat. No. 5,329,726 discloses a system for termite detection and control wherein a moisture-impermeable apertured housing is installed in the ground. The housing receives a matingly-apertured cartridge containing either a non-toxic termite attractant or a termite pesticide. This system is inoperative, however, if the cartridge is not adequately moistened. Furthermore, the system is inconvenient to use because the housing must be carefully installed and the cartridge must be routinely removed and inspected.

Certain pesticides have been investigated in the laboratory for use as termiticides. Su and others examined four pesticides, amidinohydrazone, diiodomethyl-para-tolylsulfone, chlordane, and chlorpyrifos, for the remedial control of the Formosan subterranean termite, *Coptotermes formosanus* Shiraki. Su, et al., J. Econ. Entomol. 80, 1–4 (1987); and Su, et al., J. Econ. Entomol. 81, 850–54 (1988).

Termites require a digestive cellulase in order to hydrolyze the cellulose in the wood they ingest as food. The digestive cellulase is provided either by the termite's own ventricular cells, or it is synthesized by microorganisms present in the gut of the termite. In higher termites, family Termitidae, cellulase is produced by the termite's own ventricular cells. In the four families of lower termites, Mastotermitidae, Hodotermitidae, Kalotermitidae, and Rhinotermitidae, however, flagellate protozoa found in the gut produce cellulase for digesting wood taken in by the host termites. For example, the hindgut of the Formosan subterranean termite, *Coptotermes formosanus*, contains a cellulase-producing protozoan species which hydrolyzes the cellulose in wood anaerobically via glucose to acetic acid which is then available to the termite for energy production and for lipid synthesis. Without their cellulase-producing protozoa, the lower termites are incapable of digesting sufficient sound wood to survive.

Thus, a need exists for a termite control composition that is environmentally safe and effective in preventing a termite infestation in a home while overcoming the problems of prior compositions.

According to one aspect of the present invention, such a need is satisfied by a termite control composition including a pesticide that is toxic to a termite's gut-dwelling cellulase-producing protozoa. The pesticide is present at a non-feeding-deterrent and effective pesticidal concentration. Without its protozoa, a subterranean termite of the family Rhinotermitidae is unable to digest sufficient cellulose to sustain life for more than twenty days, although during that time the termite may continue to forage and consume cellulose.

According to another aspect of the invention a method of controlling termites includes impregnating a cellulose-containing material with the termite control composition including the pesticide that is toxic to a termite's gut-dwelling cellulase-producing protozoa, and present at a non-feeding-deterrent and effective pesticidal concentration, and thereafter exposing the cellulose-containing material to termites. Foraging worker termites consume the cellulose-containing material including the pesticide and return to the colony to share the ingested cellulose-containing material and pesticide with the other members of the colony. In addition, as a form of social interaction, all of the individuals of a colony participate in the mutual exchange of food in a process known as trophallaxy. Thus, material returned to the nest by the worker termites is eventually distributed throughout the colony. As the pesticide is transmitted among the termites, the termites' gut-dwelling cellulase-producing protozoa are destroyed. Any termite lacking its cellulase-producing protozoa eventually starves to death.

According to another aspect of the invention, a cellulose-containing material is impregnated with a termite control composition that includes a chemical attractant for termites including at least one aliphatic chemical attractant and at least one aromatic chemical attractant, and a termite pesticide that is present at a non-feeding-deterrent and effective pesticidal concentration. The cellulose-containing material, impregnated with the termite control composition, is then exposed to termites. Termites respond to chemical signals such as food odor attractants or pheromones including those that elicit an alarm response or an aggregation response. Thus, by placing the cellulose-containing material impregnated with the added control composition in the soil around a structure such as a home, a homeowner can attract worker termites foraging in the area to the material impregnated with the control composition in preference to the home, so that the home remains free of termites. The worker termites consume the material with the added control composition, thus ingesting the pesticide. The concentration of the pesticide in the material is carefully adjusted to a non-feeding-deterrent yet still effective pesticidal concentration, so that the worker termites continue to consume the material. The foraging worker termites carry the ingested pesticide back to the termite colony and feed it to the other non-foraging members of the colony. The pesticide is eventually transferred to every individual in the termite colony causing maximum termite mortality. Thus, not only is the home protected from termite damage, eventually the entire termite colony is destroyed. In addition, the homeowner can easily and economically install the cellulose-containing material impregnated with the control composition.

The foregoing and other objectives, features, and advantages of the invention will be more readily understood upon consideration of the following detailed description of the invention, taken in conjunction with the accompanying drawing.

DETAILED DESCRIPTION OF THE PREFERRED EMBODIMENTS

Figure 1:
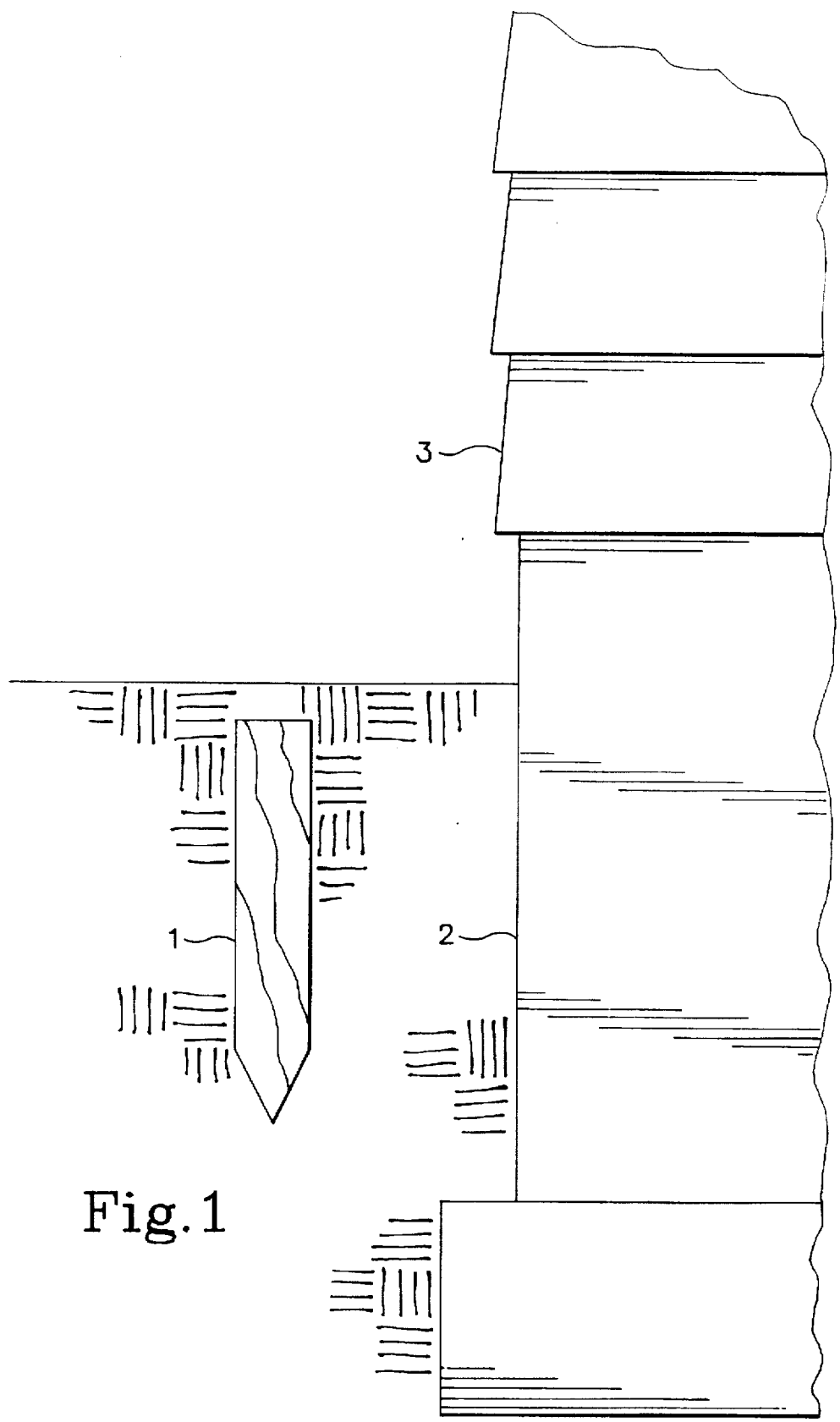
FIG. 1 is an elevational view of a wooden stake embodying the present invention shown installed proximate a home.

Referring now to an exemplary embodiment illustrated in the drawing, a method of controlling termites includes impregnating a cellulose-containing material such as a wooden stake with a termite control composition, and thereafter exposing the cellulose-containing material to termites, for example by driving the impregnated wooden stake 1 into the ground proximate the foundation 2 of a home 3. The termite control composition includes a pesticide and preferably a chemical termite attractant. To completely protect a home from termite infestation, a spaced-apart plurality of stakes are driven into the ground around the home so that a worker termite foraging anywhere in the area will be drawn to an impregnated wooden stake.

The termite control composition includes a pesticide that is toxic either to the termite's gut-dwelling cellulase-producing protozoa or to the termite itself. The pesticide is preferably one that is toxic to the termite's gut-dwelling protozoa because such pesticides are very target specific and therefore are lethal to the protozoa at concentration levels that are completely harmless to humans and other mammals. Once it has been impregnated in the cellulose-containing material, the pesticide, whether it affects the termite or its protozoa, is available only to the cellulose-ingesting termite and is harmless to all other fauna.

The concentration of the pesticide in the termite control composition is of primary importance and must be carefully adjusted and controlled. The pesticide concentration must be low enough to ensure that the foraging worker termites will not avoid or learn to avoid consuming the pesticide, and yet high enough to ensure that the pesticide retains its pesticidal action. The composition, if necessary in a carrier solvent which prevents seeding or precipitation of sparingly water-soluble compounds, is diluted to volume with water to produce an aqueous working solution. The termite control composition is added to the cellulose-containing material by immersing the material in the aqueous working solution, preferably at a pressure greater than atmospheric pressure.

A preferred pesticide that is toxic to a termite's gut-dwelling cellulase-producing protozoa is 5,7-diiodo-8-hydroxyquinoline, known as iodoquinol. The preferred concentration range in the termite control composition for iodoquinol is 50–100 ppm (wt/wt). Iodoquinol has been approved by the United States Food and Drug Administration (FDA) for pharmaceutical use in humans, and at the recommended concentration in the termite control composition poses no risk to humans.

A second preferred pesticide that is toxic to a termite's gut-dwelling cellulase-producing protozoa is di-(4-aminophenyl)-sulfone, known as dapsone. The preferred concentration range in the termite control composition for dapsone is 5–25 ppm (wt/wt). Dapsone has also been approved for pharmaceutical use in humans by the FDA, and poses no risk for humans at the recommended concentration levels.

A third preferred pesticide in the present composition is 1-methyl-4-diiodomethylsulfonyl benzene, known as diiodomethyl-para-tolylsulfone, and available as Amical from the Angus Chemical Company of Buffalo Grove, Ill. When the pesticide is diiodomethyl-para-tolylsulfone, a preferred concentration of the pesticide in the cellulose-containing material is 100–250 ppm (wt/wt). The exact effect of diiodomethyl-para-tolylsulfone on termites is not known, but it is thought that the pesticide acts by eliminating the termite's gut dwelling cellulase-producing protozoa.

The termite control composition of the present invention preferably includes a termite attractant. The termite attractant is preferably a chemical attractant such as a food odor attractant, or an aggregation attractant. An aggregation attractant causes soldier and worker termites to come to the source of the aggregation attractant. Such attractants may be produced by termites, for example to summon worker termites to repair a breach in the nest, or to summon soldier termites to the defense of the nest. One such aggregation attractant is the pheromone n-hexanoic acid.

Other attractants are food odor attractants. Many food odor attractants are related to the trail marking pheromone (Z,Z,E)-3,6,8-dodecatrien-1-ol. Aliphatic chemical compounds which are termite food odor attractants have the general structure (Z)—R—$CH_2$—CH=CH—$(CH_2)_2$—OH. These compounds have solubilities in water of less than one part per thousand (0.01%). Examples of aliphatic compounds having the general structure (Z)—R—$CH_2$—

CH=CH—(CH$_2$)$_2$—OH, which are termite food odor attractants, are set forth in Table 1.

TABLE 1

| Where R Is | Compound |
| --- | --- |
| CH$_3$— | (Z)-3-hexen-1-ol; leaf alcohol |
| CH$_3$—(CH$_2$)$_2$— | (Z)-3-octen-1-ol |
| CH$_3$—(CH$_2$)$_4$— | (Z)-3-decen-1-ol |
| CH$_3$—(CH$_2$)$_6$— | (Z)-3-dodecen-1-ol |
| (Z)—CH$_3$—CH=CH— | (Z,Z)-3,6-octadien-1-ol |
| (Z)—CH$_3$—(CH$_2$)$_2$—CH=CH— | (Z,Z)-3,6-decadien-1-ol |
| (Z)—CH$_3$—(CH2)$_4$—CH=CH— | (Z,Z)-3,6-dodecadien-1-ol |

Aromatic chemical compounds which are food odor attractants are the aromatic equivalents to the aliphatic enol compounds discussed above, where the double bond in the Z-3 position is part of an aromatic ring and the alpha hydrogens are replaced by a double-bond oxygen (=O). In general, the aromatic termite attractants are typically more soluble in water than the aliphatic termite attractants. Examples of aromatic compounds which are derivatives of benzoic acid and which are termite attractants are set forth in Table II.

TABLE II

| Substituent | Compound |
| --- | --- |
| p-HO— | 4-hydroxybenzoic acid |
| o,p-(HO—)$_2$ | 2,4-dihydroxybenzoic acid; resorcylic acid |
| m,p-(HO—)$_2$ | 3,4-dihydroxybenzoic acid; protecatechuic acid |
| m-(CH$_3$O—), p-(HO—) | 4-hydroxy-3-methoxybenzoic acid; vanillic acid |

Aromatic compounds equivalent to the dienol compounds, where the double bond in the Z-6 position or the double bonds in both the Z-3 and the Z-6 positions are part of an aromatic ring structure and the alpha hydrogens are replaced by a double-bond oxygen (=O), are also food odor attractants. The simplest members of these families are 4-ethenylbenzoic acid and 2-naphthanoic acid. In 5-phenyl-(Z)-3-penten-1-ol, the Z-6 bond is part of an aromatic ring structure.

The termite control composition of the present invention is impregnated in a cellulose-containing material. The attractant, or combination of attractants, disperses through a selected volume of soil or air in order to draw a foraging termite into a sphere of higher concentration of attractant and thus to the cellulose-containing material which is impregnated with a pesticide. In a preferred embodiment, the chemical attractant includes at least two chemical compounds having differing solubilities in water to provide a chemical attractive gradient around the impregnated cellulose-containing material. An attractant having a relatively higher solubility will disperse immediately to attract termites which may be present in already-infested areas. Such attractants include n-hexanoic acid and the aromatic food odor attractants. Such chemical compounds disperse rapidly into the area around the impregnated material, and in a short period of time they become diluted below the concentration of an effective attractant. A less soluble attractant such as one of the aliphatic food odor attractants disperses into the area around the impregnated cellulose-containing material over a longer period of time than do the aromatic food odor attractants and thus remains at an effective attractant concentration for a longer period of time.

A chemical attractant of lesser solubility such as Z-3-decen-1-ol, has a low rate of dispersion and a long residual time in the area around the impregnated material.

Thus, the dispersion of attractant from the impregnated cellulose-containing material depends upon the actual attractant composition and also upon the rate of release from the impregnated material. The cellulose-containing material preferably is impregnated with the termite control composition so that the termite control composition will be present throughout the material. Wooden chips, nominally 5 mm×10 mm×25 mm, will release all attractants rapidly. A stake, for example of dimensions 25mm×50 mm×300 mm, which is impregnated throughout its dimensions with a chemical attractant continues to provide attractant from deep within the xylem, and remains effective for an extended period of time, up to several years, depending on soil and moisture conditions. A plurality of such stakes placed in the soil 200–500 mm apart form an efficient barrier against subterranean termites by attracting the termites preferentially to the impregnated stakes.

The cellulose-containing material may be any conveniently available material such as the wooden stake 1 made, for example, of western hemlock, with dimensions 1 inch×2 inches (25 mm×50 mm). In general, termites of the Coptotermes genus forage deeper than termites of the Reticulitermes genus, and the preferred length of the stake varies according to the particular species of termite known to be a problem in the geographical area where the stake will be installed. Thus, for *Coptotermes formosanus* species the stake is about 2 feet (600 mm) long and for *Reticulitermes hesperus* (western subterranean) and *Reticulitermes flavipes* (eastern subterranean) species the stake is about 1 foot (300 mm) long.

Impregnation of the cellulose-containing material with the termite control composition may be accomplished by any convenient means. Preferably, water and water vapor are removed from the material prior to actual impregnation, for example by kiln drying or by holding the material for a period of time at a pressure less than atmospheric pressure, after which the material is immersed in the aqueous working solution of the termite control composition at a pressure greater than atmospheric pressure.

The standard full-cell wood treatment process may be used to impregnate the cellulose-containing material such as the wooden stake. The material is placed in a hermetically sealed chamber. The chamber is held under vacuum to remove all intercellular water from the material. Without allowing the entry of ambient air, the chamber is filled with a sufficient amount of an impregnating aqueous working solution to completely submerge the material. The chamber is put under pressure to force the aqueous working solution into the evacuated cells of the material. After the cells are filled the pressure is released and the solution is drained from the chamber. The chamber is evacuated to dry the material and to remove any volatile carrier solvent, leaving the cells of the material filled with the termite control composition. Typical operating conditions are set forth below.

| Stage | Pressure/Vacuum | Duration |
| --- | --- | --- |
| Evacuation | 22 in. Hg | 45 min. |
| Fill with solution | | |
| Pressure | 125 psi | 120 min. |
| Drain | | |
| Dry | 15 in. Hg | 15 min. |

The relative void volume of woods useful in the present invention, for example, western hemlock, is about 0.33. Thus, xylem occupies about 65–70% of the total volume of the wood. For such wood, the concentrations of the components of the aqueous working solution must be about twice the concentration desired in the termite control composition. If, for example, 1 cubic meter ($1\times10^9$ cc) of wood weighing $0.66\times10^9$ grams is saturated with a 1% solution of salt water, the cells will be filled with about $0.33\times10^9$ grams of solution. Once the water is evaporated, 1% of $0.33\times10^9$ grams of salt will remain in the $0.66\times10^9$ grams of wood. The final concentration of solute in the wood after treatment will be about one-half the concentration in the aqueous working solution.

A preferred termite control composition for use in an area known to be infested with termites includes the aggregation attractant, n-hexanoic acid, and a slightly soluble food odor attractant in order to attract termites foraging in the area immediately to the stake. A working solution of the selected components is prepared in water at about twice the concentration desired in the termite control composition. No carrier solvents are necessary when the food odor attractant and the pesticide are slightly soluble in water. Such a preferred termite control composition is set forth as Example 1.

EXAMPLE 1

| Component | Aqueous Solution (ppm, w/w) | Termite Composition (ppm, w/w) |
| --- | --- | --- |
| n-hexanoic acid | 100 | 50 |
| 3,4-dihydroxybenzoic acid | 30 | 15 |
| dapsone | 40 | 20 |

A preferred termite control composition for use in an area currently free from termites does not include an aggregation attractant. An attractant and a pesticide with mimimal solubility in water are preferred. Since these components are relatively insoluble, a carrier solvent such as 2-ethoxyethanol, which itself is mildly attractive to termites, is required to achieve a solution. The attractant and pesticide are first slurried in a volume of water equal to the final volume of carrier solvent, and the carrier solvent is added to the slurry to form a solution. The solution is then diluted to final volume with the remaining water. Such a preferred termite control composition is set forth below as Example 2.

EXAMPLE 2

| Component | Aqueous Solution (ppm, w/w) | Termite Composition (ppm, w/w) |
| --- | --- | --- |
| (Z)-3-decen-1-ol | 10 | 5 |
| iodoquinol | 150 | 75 |
| 2-ethoxyethanol | 10,000 | 5,000 |

A preferred termite control composition for use in an area where it is unknown if termites are present provides both immediate and long term attraction. A preferred composition is set forth as Example 3.

EXAMPLE 3

| Component | Aqueous Solution (ppm, w/w) | Termite Composition (ppm, w/w) |
| --- | --- | --- |
| n-hexanoic acid | 100 | 50 |
| 4-hydroxybenzoic acid | 20 | 10 |
| (Z)-3-octen-1-ol | 1 | 0.5 |
| (Z,Z)-3,6-octadien-1-ol | .01 | 0.005 |
| diiodomethyl-para-tolylsulfone | 400 | 200 |
| n-butanol | 10,000 | 5,000 |

The homeowner or other user may readily install the impregnated cellulose-containing material in any desired location where protection from termites is desired, such as around a home or around live wood threatened by termites. The impregnated wooden stake 1 is driven into the soil so that the entire stake is in the ground, with the top of the stake about 3–6 inches below the surface, to maximize the diffusion of the termite attractant through the surrounding soil. Preferably, the homeowner installs a series of impregnated wooden stakes proximate the foundation 2 of the home 3 around its entire perimeter, so that worker termites approaching the home from any direction will be attracted preferentially to one of the impregnated wooden stakes which they will then consume. The worker termites feed on the treated wooden stake and ingest the pesticide, which they carry back to the colony and feed to the other members of the termite colony. Since the amount of pesticide present in the impregnated wooden stake is carefully adjusted to a non-feeding-deterrent concentration, the worker termites will continue to feed on the stake. Not only will the home remain free of termite infestation, eventually the entire termite colony will be destroyed. In addition, the low level of pesticide, though fatal to the termites, is environmentally safe. The soil and the home remain free of undesirable pesticide residue.

In the continental United States, termite infestations occur primarily in homes or other wooden structures. Historically the infesting termite belongs to the family Rhinotermitidae, for example *Reticulitermes flavipes*, *Reticulitermes hesperus*, or *Reticulitermes virginicus*, known as the eastern, western, and Floridian subterranean termite, respectively. The Reticulitermes genus of termites feeds primarily on sound dead wood. Termites of the genus Coptotermes, such as *C. formosanus*, feed on sound living as well as well as on dead wood, and ravage tea bushes in India, spice forests in Indonesia, and sugar cane plantations in Guiana. In such areas, impregnated wooden stakes prepared according to the present invention may be used to protect live plants from termites.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. A termite control composition, comprising:
   (a) a pesticide that is toxic to a termite's gut-dwelling cellulase-producing flagellate protozoa after ingestion by said termite, said pesticide being lethal to said cellulase-producing flagellate protozoa and making said cellulase-producing flagellate protozoa incapable of producing cellulase, causing said termite to starve to death, said pesticide being present at a non-feeding-deterrent and effective termite $LD_{50}$, pesticidal concentration, said pesticide being selected from the group consisting of iodoguinol and dapsone; and (b) a termite attractant, said attractant being selected from the group consisting of food odor attractants and aggregation attractants.

2. The termite control composition of claim 1 wherein said termite attractant is selected from the group consisting of n-hexanoic acid, (Z)-3-hexen-1-ol, (Z)-3-octen-1-ol, (Z)-3-decen-1-ol, (Z)-3-dodecen-1-ol, (Z,Z)-3,6-octadien-1-ol, (Z,Z)-3,6-decadien-1-ol, (Z,Z)-3,6-dodecadien-1-ol, 4-hydroxybenzoic acid, 2,4-dihydroxybenzoic acid, 3,4-dihydroxybenzoic acid, 4-hydroxy-3-methoxybenzoic acid, 4-ethenylbenzoic acid, 2-naphthanoic acid, and 5-phenyl-(Z)-3-penten-1-ol.

3. The termite control composition of claim 1 wherein said termite attractant comprises n-hexanoic acid, 4-hydroxybenzoic acid, (Z)-3-octen-1-ol and (Z,Z)-3,6-octadien-1-ol.

4. The termite control composition of claim 1 wherein said composition is impregnated in a cellulose-containing material.

5. The termite control composition of claim 1 wherein said pesticide is iodoquinol.

6. The termite control composition of claim 1 wherein said pesticide is dapsone.

\* \* \* \* \*